(12) United States Patent
Winkel et al.

(10) Patent No.: US 8,053,013 B2
(45) Date of Patent: *Nov. 8, 2011

(54) FLAVOUR MODULATING SUBSTANCES

(75) Inventors: Chris Winkel, Bussum (NL); Harry Renes, Lelystad (NL)

(73) Assignee: Quest International Services B.V. (NL)

( * ) Notice: Subject to any disclaimer, the term of this patent is extended or adjusted under 35 U.S.C. 154(b) by 817 days.

This patent is subject to a terminal disclaimer.

(21) Appl. No.: 11/666,532

(22) PCT Filed: Oct. 6, 2005

(86) PCT No.: PCT/NL2005/000721
§ 371 (c)(1),
(2), (4) Date: Apr. 27, 2007

(87) PCT Pub. No.: WO2006/046854
PCT Pub. Date: May 4, 2006

(65) Prior Publication Data
US 2007/0298151 A1 Dec. 27, 2007

(30) Foreign Application Priority Data
Oct. 29, 2004 (EP) .................... 04077982

(51) Int. Cl.
A23L 1/22 (2006.01)
(52) U.S. Cl. ..................... 426/534; 426/536
(58) Field of Classification Search ................. 426/534, 426/536
See application file for complete search history.

(56) References Cited

U.S. PATENT DOCUMENTS

| | | | |
|---|---|---|---|
| 5,624,906 | A | 4/1997 | Vermeer |
| 6,287,620 | B1 | 9/2001 | Van Den Ouweland et al. |
| 6,956,029 | B1 * | 10/2005 | Maier et al. ............. 514/62 |
| 2003/0143661 | A1 * | 7/2003 | Lorbert et al. ............ 435/68.1 |
| 2004/0071855 | A1 | 4/2004 | Wassenaar |
| 2004/0072254 | A1 | 4/2004 | Callamaras et al. |
| 2005/0013846 | A1 | 1/2005 | Pelan et al. |
| 2009/0169696 | A1 * | 7/2009 | Renes et al. ............. 426/534 |

FOREIGN PATENT DOCUMENTS

| | | |
|---|---|---|
| DE | 297 167 A5 | 1/1992 |
| EP | 1 291 342 A1 | 3/2003 |
| EP | 1 401 500 | 3/2004 |
| FR | 2 757 180 A1 | 6/1998 |
| GB | 1 420 909 | 9/1974 |
| GB | 2 396 414 A | 6/2004 |
| WO | 90/06689 A1 | 6/1990 |
| WO | 92/06601 A1 | 4/1992 |
| WO | 97/04667 A1 | 2/1997 |
| WO | 01/77292 A2 | 10/2001 |
| WO | 02/100192 A1 | 12/2002 |
| WO | 03/049696 A2 | 6/2003 |
| WO | 2004/055048 A2 | 7/2004 |
| WO | 2004/075633 A1 | 9/2004 |

OTHER PUBLICATIONS

NPL from "Chemical Book.com" showing chemical structure of Glucosamine, retrieved Oct. 7, 2009.*
B. Lindemann, "Receptors and Transduction in Taste", Nature, Sep. 13, 2001, pp. 219-225, vol. 413.
(MSG) H. Suzuki et al., "Improvement of the bitter Taste of Amino Acids Through the Transpeptidation Reaction of Backerial γ-Glutamyltranspeptidase", J. Agric. Food Chem., 2002, pp. 313-318, vol. 50, No. 2.
K. Shima et al., "Novel Brothy Taste Modifier Insolated from Beef Broth", J. Agric Food Chem., 1998, pp. 1465-1468, vol. 46, No. 4.
Y. Ueda et al., "Flavor Characteristics of Glutathione in Raw and Cooked Foodstuffs", Biosc. Biotech. Biochem., 1997, pp. 1977-1980, vol. 61, No. 12.
A. N. Pronin et al., "Identification of Ligands for Two Human Bitter T2R Receptors",Chemical Senses, 2004, pp. 583-593, vol. 29.
P. A. Breslin, "Interactions Among Salty, Sour and Bitter Compounds", Trends in Food Science and Technology, Dec. 1996, pp. 390-399, vol. 7.
M. Cliff et al., "Descriptive analysis of Oral Pungency", J Sensory Studies, Feb. 24, 1992, pp. 279-290, vol. 7.
P. Dalton et al., The Merging of the Senses: Integration of Subthreshold Taste and Smell, Nature Neurosci., May 2000, pp. 431-432, vol. 3, No. 5. Database Beilstein, Beilstein Crossfire Institut Zur Foerderung der Chemischen Wissenschaften; BRN 8218971, "Acetic acid (2,4,5-trihydroxy-6-hydroxymethyl-tetrahydro-pyran-3-ylcarbamoyl)-methyl ester" Feb. 29, 2000, XP002379570, Abstract.
Database Beilstein, Beilstein Crossfire Institut Zur Foerderung der Chemischen Wissenschaften; BRN 7137987, "3- hydroxy-2-(2,3,4,5,6-pentahydroxy-hexanoylamino)-propionic acid" Jul. 28, 1995, XP002379571, Abstract.

(Continued)

*Primary Examiner* — Chhaya Sayala
*Assistant Examiner* — Jenna A Watts
(74) *Attorney, Agent, or Firm* — The Webb Law Firm

(57) ABSTRACT

The present invention in a first aspect relates to novel flavour modulating substances according to formula (I) or formula (II) or edible salts thereof or both: $R^1$—$CR^2(OR^3)$—CO—$NR^4$—$CHR^5R^6$ (I). It was found that substances represented by formula (I) or formula (II) can advantageously be used to impart desirable flavour, especially taste attributes to foodstuffs, beverages, pharmaceutics, tobacco products and oral care products they are incorporated in. In addition these substances are capable of modulating and complementing the sensory impact of other, flavour imparting, substances. Thus, the present flavour modulating substances are advantageously applied in flavour compositions, foodstuffs, beverages, pharmaceutics and oral care products. Typical examples of flavour modulating substances according to the present invention include N-lactoyl glucosamine, N-lactoyl glucosaminic acid, N-gluconyl glucosamine, N-gluconyl glucosaminic acid, hemiacetals or lactones thereof, edible salts thereof and mixtures thereof.

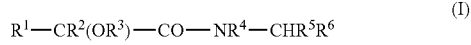

(I)

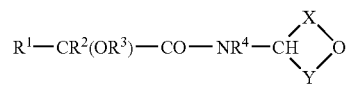

(II)

1 Claim, No Drawings

OTHER PUBLICATIONS

Database Biosis [Online], Biosciences Information Service, Philadelphia, PA, US; 1989, Valcavi U. et al., "New Potential Immunoenhancing Compounds Synthesis and Pharmacological Evaluation of New Long-Chain 2 Amido-2-Deoxy-D-Glucose Derivatives", XP002379572, Database accession No. PREV199089051988 Abstract.

Valcavi et al., "New Potential Immunoenhancing Compounds", Arzneimittel-Forschung, 1989, pp. 1190-1195, vol. 39, No. 10, ISSN: 0004-4172.

Kuboki et al., "An Expeditious Route to N-Glycolylneuraminic Acid Based on Enzyme-Catalyzed Reaction", Tetrahedron, Feb. 17, 1997, pp. 2387-2400, XP004105332, ISSN: 0040-4020, pp. 2392-2393; compounds 2A, 2C, 3A, 3C, vol. 53, No. 7, Elsevier Science Publishers, Amsterdam, NL.

Chenault et al., "Kinetic Resolution of Unnatural and Rarely Occurring Amino Acids: Enantioselective Hydrolysis of N-Acyl Amino Acids Catalyzed by Acylase I", Journal of the American Chemical Society, Aug. 2, 1989, pp. 6354-6364, vol. 111, No. 16, XP000940668, ISSN: 0002-7863, p. 6357, left-hand column, paragraph 4; compounds 22-MA, American Chemical Society, Washington, DC.

Fialova et al., "Hydrolytic and Transglycosylation Reactions of N-Acyl Modified Substrates Catalysed by Beta-N-Acetylhexosaminidases", Tetrahendron, Jan. 12, 2004, pp. 693-701, vol. 60, No. 3, XP004482884, ISSN: 0040-4020, compounds 5, 5A, 5B, 5C, Elsevier Science Publishers, Amsterdam, NL.

Database Beilstein, Beilstein Crossfire Institut Zur Foerderung der Chemischen Wissenschaften; BRN 1715054, "2-(2,4-dihydroxy-3,3-dimethyl-butyrylamino)-succinic acid", Nov. 22, 1993, XP002379573, Abstract.

Database Beilstein, Beilstein Crossfire Institut Zur Foerderung der Chemischen Wissenschaften; BRN 1714863, "2-hydroxy-N-(2,4,5-trihydroxy-6-trihydroxy-6-hydroxymethyl-tetrahydro-pyran-3-yl)-propionamide", Sep. 20, 1991, XP002379574, Abstract.

Database Beilstein, Beilstein Crossfire Institut Zur Foerderung der Chemischen Wissenschaften; BRN 9556029, "3-hydroxy-2-(2-hydroxy-3-methyl-butyrylamino)-propionic acid", Apr. 23, 2004, XP002379575, Abstract.

Chen et al., "P3 Cap Modified Phe*-Ala Series BACE Inhibitors", Bioorganic & Medicinal Chemistry Letters, Jan. 5, 2004, vol. 14, No. 1, Jan. 5, 2004, pp. 245-250, XP002379562, ISSN: 0960-894X.

Database Medline [Online], US National Library of Medicine (NLM), Bethesda, MD, US; Sep. 1988, Horiuchi, T. et al., "Purification and Properties of N-Acyl-D-Mannosamine Dehydrogenase from *Flavobacterium* sp. 141-8", XP002379576, Database Accession No. NLM3240988.

Horiuchi et al., "Purification and Properties of N-Acyl-D-Mannosamine Dehydrogenase from *Flavobacterium* sp. 141-8", Abstract and Journal of Biochemistry, Sep. 1988, vol. 104, No. 3, pp. 466-471, ISSN: 0021-924X.

Schneider et al., "Verknuepfung Von Zuckern Mit Aminosaeureestern Lipophiler Alkohole Zu Grenzflaechenaktiven Zuckerderivaten", Hoppe-Seyler's Zeitschrift Fuer Physiologische Chemie, Walter De Gruyter, Berlin, DE, 1963, vol. 330, pp. 182-188, XP001021387, ISSN: 0018-4888, pp. 184-188.

* cited by examiner

FLAVOUR MODULATING SUBSTANCES

BACKGROUND OF THE INVENTION

1) Field of the Invention

The present invention concerns flavour improvement in foodstuffs, beverages, pharmaceutics and oral care products. More particularly, the present invention provides novel flavour modulating substances and flavour compositions comprising said flavour modulating substances that can be used to confer a fuller and richer taste and/or aroma to foodstuffs, beverages, pharmaceutics and oral care products. The present invention also encompasses the use of the aforementioned substances for improving the flavour of foodstuffs, beverages, pharmaceutics and oral care products, as well as to foodstuffs, beverages, pharmaceutics and oral care products containing these substances.

2) Description of the Related Art

The flavour of foodstuffs and beverages consists of two parts: the aroma and the taste. In general what is perceived through the olfactory epithelium in the nasal cavity is referred to as 'aroma', whereas the term 'taste' is generally used to describe the sensory impact that is perceived via the mouth, especially the tongue. The sense of taste provides the final analysis of food prior to ingestion thereof. Visual and olfactory signals already give a first indication but only after intake of the food into the mouth the final decision is made either to ingest or to reject the food. Sweet taste is usually a signal that the food is safe (nice) leading to ingestion of the food. The 'reactions' to salt and umami are really dependent on the strength of the signal. Bitter and sour are usually repulsive taste sensations, leading to rejection. Temperature is another measure by which the food is judged just as well as aching sensations like capsaicin (hot pepper) and certain chemicals (like carbon dioxide).

In short this means that taste is a very crucial and very complex system. Until recently most flavour research was focused towards aroma. Especially the last years a series of publications relating to molecules with a (positive) contribution to the taste of foodstuffs has emerged.

Such research has been stimulated significantly by the fact that quite some receptors which are involved in the different taste sensations have been characterized by now (B. Lindemann; Nature 413, 219 (2001)).

Several screening systems have been described that make it possible to screen, in a short time, large series of molecules for their (modulating) effect on taste response (cf. WO04055048, GB2396414, WO0177292 and US2004/0072254).

It is remarkable that most research on these taste modulating molecules so far has been devoted to taste enhancement in savoury products. Several, mainly Japanese, publications describe umami molecules, i.e. alternatives to mono sodium glutamate (MSG) (H Suzuki et al, J Agric Food Chem 50, 313-318 (2002); K Shima et al, J Agric Food Chem 46, 1465-1468 (1998); Y Ueda et al, Biosc Biotech Biochem 61 1977 (1997)).

In EP 1291342 a 'general taste enhancer' is disclosed that was reported to be suitable for enhancing sweetness as well.

In patent applications WO9704667 and WO04075633 tripeptides and amino acid condensates with lactic acid and succinic acid are described that have both their own taste as well as some enhancing properties. Alpha keto acids are reported to give body and mouthfeel to foodstuffs they are added to (U.S. Pat. No. 6,287,620).

Chlorogenic acids are claimed to enhance sweetness and to reduce bitterness (WO02100192).

In sweet and beverage products, further examples of the importance of the gustative dimension of flavourings have been reported, including bitterness, tingling and cooling-freshness.

Bitterness is an essential aspect of some food flavours, among which chocolate taste. Purine alkaloids, like theombromine and caffeine, as well as amino acids and peptides have been known for a long time as bitter compounds. In British patent no. GB 1420909 it is disclosed that the bitter flavour of cocoa can be reproduced using a combination of a purine alkaloid and an amino acid or an oligopeptide which 'produces a surprisingly more natural simultaneously bitter and astringent flavour note than either of these types of substances alone'.

Quite a bit of work has been devoted to find bitter taste suppressors (A. N. Pronin et al, Chemical Senses 29, 583-593 (2004); EP1401500; P. A. Breslin, Trends in Food Science & Technology 7, 390-399 (1996)).

Menthol, an important constituent of peppermint oil, has a strong impact on flavoured products not only because of its mint smell but also because it imparts a cooling, fresh taste. Next to mint flavoured products, the use of menthol in other types of flavour to impart a cool taste has been suggested. US patent application no. 2005/013846, for example, discloses how menthol and derivatives thereof can be used as flavouring in water continuous spreadable acidified food products to obtain table spreads exhibiting a fresh, cool taste impression.

Similarly, cinnamic aldehyde and eugenol, constituents of cinnamon oil, are used in flavouring composition for confectionery products, not only for their smell but also because they impart a warm and piquant-tingling taste. The oral pungency of cinnamic aldehyde was described as burning and tingling by Cliff M and Heymann H [Journal of Sensory Studies 7 (1992) 279-290]. According to the same authors eugenol exhibits a long-lasting numbing effect. Cinnamon oil has been proposed as a taste improving flavouring. International patent application no. WO 90/06689 discloses that cinnamon oil, among other spice extracts, added to a minty flavour formulation, can be used to improve the long-lasting flavour of chewing-gum.

Another interesting aspect of taste is that it can have an impact on aroma. It was reported that people having artificially sweetened water in their mouth were significantly more sensitive to the smell of benzaldehyde than people having plain water in their mouth (P Dalton et al, Nature Neurosci. 3, 431-432 (2000).

The aim of the present invention is to provide new so-called 'flavour modulating substances' that provide a positive contribution to the overall flavour impression of foodstuffs, beverages, oral care products and/or pharmaceutics in which they are incorporated.

SUMMARY OF THE INVENTION

The present inventors have surprisingly found that substances represented by the following formula (I) as well as substances that are formed by internal cyclisation reactions thereof and that are represented by the following formula (II), and edible salts of the substances according to both formulae can be used advantageously for modulating the flavour of foodstuffs, beverages, pharmaceutics and oral care products:

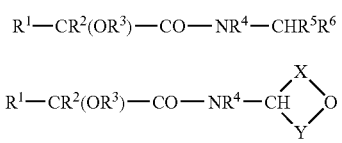

The flavour modulating substances according to the present invention can be applied advantageously to impart desirable flavour attributes, especially taste attributes, to the aforementioned products. In addition, the present flavour modulating substances are capable of modulating the taste and/or aroma impact of other flavour ingredients contained within these same products, thereby improving the overall flavour quality of these products.

Prior art documents WO 92/06601, FR 2 757 180 and DD 297 167 all disclose derivatives of α-hydroxy carboxylic acids and 1-deoxy-1-amino aldoses, which are not encompassed by present formula (I) or (II). According to WO 92/06601 such derivatives possess similar physical rheological and colligative properties to sucrose and may therefore be used as sugar substitutes for simulating the structure, texture, freezing point depression, moisture retention, density, water solubility, solution viscosity properties, stability, non-reactivity and appearance characteristics of sucrose. According to WO 92/06601 said sugar substitute may have the sweetness potency of 0% to 100% of that of sucrose. Further remarks or references regarding the flavour characteristics of said derivatives were not found in any one of these prior art documents.

Thus, the present invention relates to substances according to formula (I) and/or formula (II). Furthermore, the invention relates to flavour compositions, foodstuffs, beverages, pharmaceutics and oral care products, comprising one or more substances according to these formulae and/or edible salts thereof.

Other aspects of the present invention relate to the use of one or more substances according to formula (I), formula (II) and/or edible salts thereof for improving the flavour of foodstuffs, beverages and pharmaceutics, and to a process for improving the flavour of the latter products.

DETAILED DESCRIPTION OF THE INVENTION

Accordingly, the present invention in a first aspect relates to flavour modulating substances according to formula (I) or formula (II) and edible salts thereof:

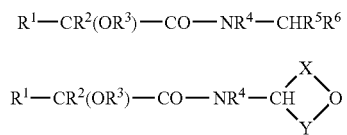

Wherein:
$R^1$ and $R^2$ independently represent hydrogen; $C_1$-$C_8$ alkyl, $C_2$-$C_8$ alkenyl or $C_3$-$C_8$ cycloalkyl, each optionally substituted with 1-8 substituents selected from hydroxyl, oxo, $C_1$-$C_3$ alkoxyl, $C_1$-$C_3$ acyl, $C_1$-$C_3$ alkyl; $C_2$-$C_3$ alkenyl and $C_1$-$C_3$ carboxyl;

$R^3$ represents hydrogen, $C_1$-$C_3$ acyl or $C_1$-$C_3$ alkyl;
$R^4$ represents hydrogen; $C_1$-$C_6$ alkyl, $C_2$-$C_6$ alkenyl, $C_1$-$C_3$ acyl, $C_3$-$C_6$ cycloalkyl, $C_3$-$C_6$ cycloalkenyl or $C_1$-$C_6$ acyl, each optionally substituted with 1-6 substituents selected from hydroxyl, $C_1$-$C_3$ alkyl and $C_2$-$C_3$ alkenyl;
$R^5$ represents hydrogen, formyl or $C_1$ carboxyl;
$R^6$ represents $C_1$-$C_6$ alkyl wherein each carbon atom is substituted with a substituent independently selected from hydroxyl, oxo, $C_1$-$C_3$ alkoxyl, and $C_1$-$C_3$ acyl;
X represents —CHOH— or —CO—;
Y represents a moiety according to the formula —(CHOH)$_n$—CHR$^9$— wherein n is 1 or 2 and wherein $R^9$ represents hydrogen or $C_1$-$C_4$ alkyl wherein each carbon atom is substituted with a substituent selected from hydroxyl, oxo, $C_1$-$C_3$ alkoxyl, and $C_1$-$C_3$ acyl;
provided that if $R^5$ represents hydrogen $R^6$ comprises an oxo substituent.

Thus, the present flavour modulating substance is a derivative of an α-hydroxy carboxylic acid and a primary amine, said primary amine further at least comprising an aldehyde, keto or carboxylic acid moiety.

The present inventors have found that the above-mentioned substances are very useful ingredients which, particularly in the presence of other flavouring substances, are capable of imparting highly appreciated taste sensations to the products in which they are incorporated, specifically a quite remarkable "roundness", "fullness", "substance", "continuity", "metallic", "bloody", "raw meat" and/or "long lasting". Because of this, the present flavour modulating substances can be employed to improve the taste (including "mouthfeel") of foodstuffs, beverages, pharmaceutics and oral care products. The taste improving substances of the present invention as such are capable of imparting highly desirable taste attributes. In addition, it has been found that the flavour modulating substances according to the invention are capable of complementing and modifying the sensory impact of other, flavour imparting, substances contained in the aforementioned products.

The term "flavour modulating" as used herein refers to the capability of a substance to alter the taste and/or aroma impact of other, flavour imparting, substances present within the same product, with the proviso that this change in taste impact is not caused by a flavour contribution of said substance per se, but instead that it mainly results from the combined effect of on the one hand the flavour modulating substance and on the other hand the other, flavour imparting, substances. The present substances combine the capability of modifying the taste of other flavour substances with a taste contribution of their own. The favourable impact of the present taste improving substances is believed to be the result of the combination of these two effects.

Because the flavour modulating substances according to the invention are not particularly volatile, they do not produce a strong aroma impact, even though they do affect the aroma impact of other, flavour imparting, substances. Here the term "aroma" refers to the aspect of flavour that is perceived through the olfactory epithelium. Because of the low volatility of the present flavour modulating substances it is believed that the advantageous properties of these substances are somehow associated with the impact that these substances have on the sensory receptors located within the mouth.

It was found that particularly satisfying results can be obtained with flavour modulating substances according to formula (I) and/or formula (II) wherein $R^1$ represents $C_2$-$C_6$ alkyl or $C_4$-$C_6$ cycloalkyl, wherein each carbon atom is substituted with a substituent independently selected from hydroxyl, oxo, carboxyl, $C_1$-$C_3$ alkoxyl and $C_1$-$C_3$ acyl. Even more preferably, $R^1$ represents $C_2$-$C_6$ alkyl, wherein each carbon atom is substituted with a single hydroxyl group. Most preferably, $R^1$ represents $C_3$-$C_5$ alkyl, wherein each carbon atom is substituted with a single hydroxyl group. Hence, according to this embodiment $R^1$—$CR^2(OR^3)$—CO— preferably represents the residue of an aldonic acid, more preferably a $C_5$ or $C_6$ aldonic acid.

Alternatively, in another preferred embodiment $R^1$ represents $C_1$-$C_4$ alkyl, more preferably $C_1$-$C_2$ alkyl, most preferably methyl.

In the aforementioned formula (I) and/or formula (II) $R^2$ preferably represents hydrogen or $C_1$-$C_4$ alkyl, most preferably hydrogen. Likewise, $R^3$ preferably represents hydrogen or $C_1$-$C_3$ alkyl or acyl, most preferably it represents hydrogen.

In formula (I) and/or in formula (II), $R^4$ preferably represents hydrogen.

According to another preferred embodiment $R^6$ represents $C_3$-$C_5$ polyhydroxyalkyl, $C_3$-$C_5$ polyhydroxy-carboxyalkyl or $C_3$-$C_5$ polyhydroxyalkanal such that the present flavour modulating substance is a derivative of on the one hand an α-hydroxy carboxylic acid and on the other hand an aminated aldose, aminated aldonic acid or aminated uronic acid, wherein the amino group is attached to the β carbon atom or to the terminal carbon atom of said aminated aldose, aminated aldonic acid or aminated uronic acid.

According to a particularly preferred embodiment a substance according to formula (I) is provided wherein $R^5$ represents formyl and wherein $R^6$ represents $C_3$-$C_4$ alkyl wherein each carbon atom is substituted with a single hydroxyl group.

More preferably, in said formula —$NR^4$—$CHR^5R^6$ represents the residue of 2-deoxy-2-amino-aldose (aldosamine). Even more preferably —$NR^4$—$CHR^5R^6$ represents the residue of a hexosamine or pentosamine. Most preferably —$NR^4$—$CHR^5R^6$ represents the residue of glucosamine, galactosamine, mannosamine, xylosamine, lactosamine, ribosamine or arabinosamine, most preferably glucosamine, galactosamine or mannosamine.

In case flavour modulating substances are provided wherein —$NR^4$—$CHR^5R^6$ represents the residue of an aldosamine, intramolecular nucleophilic addition can take place between a hydroxyl group and the carbonyl group of the same molecule, resulting in the formation of a cyclic hemiacetal. Cyclic hemiacetals comprising a five or six membered ring are the most favourable, because these rings are essentially unstrained.

Accordingly, in a preferred embodiment flavour modulating substances according to formula (II) are provided wherein X represents —CHOH—, and $R^9$ represents hydrogen or $C_1$-$C_2$ alkyl wherein each carbon atom is substituted with a single hydroxyl group. More preferably in said formula n=1 and $R^9$ represents $C_1$-$C_2$ alkyl wherein each carbon atom is substituted with a single hydroxyl group, or n=2 and $R^9$ represents hydrogen or hydroxymethyl. Even more preferably n=2 and $R^9$ represents hydroxymethyl, such that a cyclic hemiacetal of a hexosamine is provided comprising a six membered ring. Preferably in said formula,

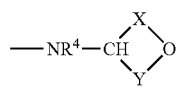

represents the residue of a hemiacetal of a hexosamine selected from glucosamine, galactosamine and mannosamine.

In another equally preferred embodiment $R^5$ in formula (I) represents a $C_1$ carboxylic acid and $R^6$ represents $C_3$-$C_4$ alkyl wherein each carbon atom is substituted with a single hydroxyl group. More preferably in said formula —$NR^4$—$CHR^5R^6$ represents the residue of 2-deoxy-2-amino-aldonic acid (aldosaminic acid). Even more preferably —$NR^4$—$CHR^5R^6$ represents the residue of a hexosaminic acid or a pentosaminic acid. Most preferably —$NR^4$—$CHR^5R^6$ represents the residue of a hexosaminic acid selected from the group of glucosaminic acid, galactosaminic acid and mannosaminic acid.

In case flavour modulating substances are provided according to formula (I) wherein $NR^4$—$CHR^5R^6$ represents the residue of an aldosaminic acid, the carboxyl and hydroxyl group within the same molecule can form a lactone ring. In fact the formation of a five or six membered lactone ring is highly favoured in molecules wherein a carboxyl group and a hydroxyl group are separated by three or four carbon atoms.

Accordingly, in a preferred embodiment flavour modulating substances according to formula (II) are provided wherein X represents —CO— and $R^9$ represents hydrogen or $C_1$-$C_2$ alkyl wherein each carbon atom is substituted with a single hydroxyl group. More preferably in said formula n=1 and $R^9$ represents $C_1$-$C_2$ alkyl wherein each carbon atom is substituted with a single hydroxyl group, or n=2 and $R^9$ represents hydrogen or hydroxymethyl. Even more preferably n=2 and $R^9$ represents hydroxymethyl, such that the lactone of a hexosaminic acid is provided comprising a six membered ring. Most preferably in said formula,

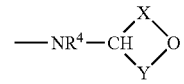

represents the residue of a lactone of a hexosaminic acid selected from glucosaminic acid, galactosaminic acid and mannosaminic acid.

In a particularly preferred embodiment the present flavour modulating substances are selected from the group of N-lactoyl glucosamine, N-lactoyl glucosaminic acid, N-gluconyl glucosamine, N-gluconyl glucosaminic acid, hemiacetals or lactones thereof, edible salts thereof and mixtures thereof. Most preferably the flavour modulating substance is N-lactoyl glucosamine.

Another aspect of the invention relates to compositions comprising at least 0.001 ppm (parts per million), preferably at least 0.01 ppm, more preferably at least 0.05 ppm, most preferably at least 0.1 ppm of one or more of the present flavour modulating substances. According to a particularly preferred embodiment, the aforementioned composition is a flavour compositions comprising at least 0.1 wt % of flavouring substances and one or more of the flavour modulating substances in an amount of at least 0.001 wt. %, preferably at least 0.01 wt. %. Most preferably, the flavour composition contains at least 0.1 wt. % of the present flavour modulating substances. Preferably the amount of the present flavour modulating substances does not exceed 80 wt. %, more preferably it does not exceed 40 wt. %. Here the term "flavouring substance" refers to any substance that is capable of imparting a detectable flavour impact, especially at a concentration below 0.1 wt. %, more preferably below 0.01 wt. %. In a preferred embodiment the flavour composition according to the invention comprises a flavouring substance in an amount of at least 0.5 wt. %, preferably at least 1 wt. %, based on the total weight of the composition.

Typically, in the present flavour composition, the flavour modulating substances and flavouring substances as defined herein before are employed in a weight ratio within the range of 10:1 to 1:100, preferably in a weight ratio of 5:1 to 1:50.

The flavour composition according to the present invention may suitably be prepared in the form of a liquid, a paste or a powder. In a particularly preferred embodiment the flavour composition is a free flowing powder.

Typical examples of flavour compositions according to the present invention include savoury flavourings, especially meat flavourings; dairy flavourings and berry flavourings.

In one preferred embodiment flavouring compositions are provided comprising N-Lactoyl glucosamine as well as a savoury flavouring, preferably a meat flavouring.

In another preferred embodiment the present composition is a product selected from the group consisting of foodstuffs, beverages, pharmaceutics and oral care products, said product comprising at least 0.001 ppm, more preferably at least 0.01 ppm, still more preferably 0.1 ppm, still more preferably at least 0.5 ppm, most preferably at least 1.0 ppm of one or more flavour modulating substances according to formula (I) and/or formula (II) or edible salts thereof. Typically, the aforementioned products will contain the flavour modulating substances in a concentration of not more than 1000 ppm, preferably of not more than 500 ppm.

Typical examples of foodstuffs according to the present invention include soups, sauces, stocks, bouillons, cheese products, dressings, seasonings, margarines, shortenings, bread, pastry, noodles, dairy products and beverages. The benefits of the present invention may also be realised in oral care products such as toothpaste and mouthwash.

Yet another aspect the present invention relates to a process of improving the flavour of a foodstuff, a beverage, a pharmaceutical product or an oral care product, comprising incorporating into said foodstuff, beverage, pharmaceutical product or oral care product one or more flavour modulating substances according to formula (I) and or formula (II) and/or edible salts thereof, in an amount of at least 0.001 ppm, preferably of at least 0.01 ppm.

The flavour modulating substances according to formula (I) and formula (II) can suitably be produced by reacting a primary or secondary amine with an α-hydroxycarboxylate. Thus, yet another embodiment of the present invention relates to a process of producing flavour modulating substances, comprising the step of reacting an amine substance according to below formula (III) or formula (V) or salts thereof with an α-hydroxycarboxylate according to formula (IV) or a salt thereof:

  (III)

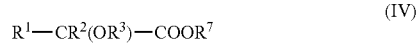  (IV)

  (V)

wherein X, Y, $R^1$, $R^2$, $R^3 R^4$, $R^5$ and $R^6$ have the same meaning as defined above in relation to formula (I) and (II); and wherein $R^7$ represents hydrogen or $C_1$-$C_3$ alkyl, preferably hydrogen. The invention also encompasses reacting an amine substance as defined herein before with a lactone that is formed by internal esterification of a substance according to formula (IV) wherein $R^1$ and/or $R^2$ contain a hydroxyl group.

Typically, the aforementioned process is carried out by first preparing a mixture of (i) one or more of the amine substances and (ii) one or more α-hydroxycarboxylates (including salts thereof); followed by heating said mixture. In a preferred embodiment, the mixture contains at least 10 wt. %, preferably at least 20 wt. % and most preferably at least 30 wt. % of the α-hydroxycarboxylates and/or salts thereof. The amine substances represented by formula (III) or (V) and/or salts thereof are typically present in the mixture in a concentration of at least 1 wt. %, preferably of at least 5 wt. %, more preferably in a concentration of at least 15 wt. %.

The present invention, in another embodiment, encompasses flavour modulating compositions obtainable by the processes described above, flavouring compositions comprising these and the use thereof for modulating the flavour of foodstuffs, beverages, pharmaceutics or oral care products.

According to a particularly preferred embodiment of the present process, the reaction of a primary or secondary amine with an α-hydroxycarboxylate is carried out in the presence of a carbohydrate source. Typically, the reaction is carried out by first preparing a mixture of (i) one or more of the amine substances; (ii) one or more of the α-hydroxycarboxylates; and the carbohydrate source, followed by heating said mixture. Preferably, the carbohydrate source is incorporated in the mixture in a concentration of at least 0.5 wt. %, more preferably of at least 1 wt. %.

In a particularly preferred embodiment of the present process a Maillard flavour preparation, preferably a process flavour, is produced by heating a mixture of (i) a carbohydrate source; (ii) a nitrogen source, said nitrogen source comprising 0.5-100 wt %, preferably 5-100 wt %, most preferably 10-100 wt %, of the one or more amine substances and (iii) one or more of the α-hydroxycarboxylates.

The combination of nitrogen source and carbohydrate source preferably represents at least 1 wt. % of the mixture before it is heated. More preferably, said mixture represents at least 5 wt. % and most preferably at least 15 wt. % of the mixture. Maillard flavour preparations obtained by said process will typically comprise one or more of the present flavour modulating substances. Thus, the aforementioned process preferably yields a Maillard flavour preparation comprising 0.0001-0.01 wt %, preferably 0.0001-0.001 wt % of one or more substances according to formula (I) or (II) or salts thereof.

The term "Maillard flavour preparation" as used herein refers to a flavour preparation which is obtained by heating a mixture of ingredients including a nitrogen source, preferably amino nitrogen, and a carbohydrate source, preferably a reducing sugar. The terms "process flavour" or "reaction flavour" which are used interchangeably herein refer to compositions or products obtained by heat processing together a protein nitrogen source and a carbohydrate source, at a temperature, preferably, not exceeding 180° C. In the present process it is particularly preferred to heat the combination of carbohydrate source, nitrogen source and liquid phase to a temperature of between 60-180° C., even more preferably between 100-140° C. According to a preferred embodiment the heating is carried out for a period of 0.1-8 hours, preferably of 0.5-7 hours.

According to a particularly preferred embodiment the α-hydroxycarboxylates and/or salts thereof are present in the mixture as a continuous liquid phase. The term "liquid" as used herein in relation to the continuous liquid phase refers to the fact that, especially under the heating conditions employed, the continuous phase exhibits fluid or flowing behaviour. Furthermore, it should be understood that the term liquid embraces emulsions and suspensions.

According to a preferred embodiment of the present invention the process is performed in a continuous liquid phase containing at least 40 wt %, more preferably at least 45 wt %, most preferably at least 50 wt % of the α-hydroxycarboxylate. The present continuous liquid phase advantageously comprises water in an amount sufficient to liquefy the α-hydroxycarboxylate, e.g. in an amount of at least 2 wt. %, even more preferably at least 5 wt. %. It is preferred that the amount of water does not exceed 70 wt. %, based on the total weight of the continuous liquid phase, preferably it does not exceed 60 wt. %, more preferably it does not exceed 45 wt. %.

Preferably the said continuous liquid phase comprises an α-hydroxycarboxylic acid, such as lactic acid, malic acid, tartaric acid, citric acid, ascorbic acid, gluconic acid, glucuronic acid and galacturonic acid or a salt thereof. In a particularly preferred embodiment the α-hydroxycarboxylic acid component is selected from lactic acid, lactic acid salts, gluconic acid, gluconic acid salts and mixtures thereof, still more preferably from lactic acid, gluconic acid and mixtures thereof.

In a particularly preferred embodiment the continuous liquid phase comprises, based on the total weight of the continuous liquid phase, an amount of water of between 2-30 wt %, more preferably 5-20 wt. %, most preferably 5-15 wt %, and lactic acid in an amount of at least 10 wt %, more preferably at least 30 wt %, most preferably at least 50 wt %.

In another particularly preferred embodiment the continuous liquid phase comprises, based on the total weight of the composition, an amount of water of between 20-70 wt %, more preferably 30-60 wt. %, most preferably 40-55 wt %, and gluconic acid in an amount of at least 10 wt %, more preferably at least 30 wt %, most preferably at least 45 wt %.

The carbohydrate source can be any type conventionally used in the field of process flavours and Maillard flavour preparations. Preferably the carbohydrate source comprises a reducing sugar. Non-limiting examples include ribose, xylose, glucose, fructose, rhamnose, lactose, maltose and sucrose.

The present "nitrogen source", besides the amine substances represented by the aforementioned formula (III) or (V), may furthermore comprise a protein nitrogen source, autolyzed yeasts, peptides, amino acids and/or their salts, decarboxylated amino acids, nucleosides, nucleotides, salts thereof and mixtures thereof.

In a preferred embodiment of the present process the nitrogen source and the carbohydrate source are employed in a weight ratio within the range of 1:20 to 20:1. In another preferred embodiment the employed weight ratio of α-hydroxycarboxylates and/or salts thereof relative to the combination of carbohydrate source and nitrogen source is within the range of 1:1 to 20:1, more preferably within the range of 2:1 to 10:1.

The invention is further illustrated by means of the following examples.

EXAMPLES

Example 1

N-Lactoyl-Glucosamine

Lactic acid (30 g) and glucosamine (10 g) were mixed and heated for 4 hours at 120° C. The reaction mixture was cooled and washed with ethyl acetate. The residue (25 g) was dissolved in 100 g of water.

NMR showed that at least 10% of the reaction mixture was N-lactoyl-glucosamine. Subsequently 30 g of maltodextrin (MD 10) and 10 g of salt were added and the slurry was spray-dried.

Example 2

Preparation of a Liquid Process Flavour Containing N-Lactoyl-Glucosamine 75 g of lactic acid (90% pure) was mixed with 22.5 g of glucosamine.HCl and 2.5 g of Dextrose. The mixture was reacted at 120 C for 4 hours. The reacted mixture was cooled down and stored at 4 C.

Example 3

Preparation of a Process Flavour Powder Containing N-Lactoyl-Glucosamine 30 g of liquid product as described in example 2 was dissolved in 120 g of water. The pH of the solution was adjusted to 6 with 50% NaOH solution. Finally 60 g of maltodextrin (with a dextrose equivalent of 10) and 30 g of NaCl were dissolved in the solution. The viscous liquid obtained was then spray-dried to get a powder flavour ingredient containing N lactoyl glucosamine.

Example 4

Preparation of Pure N-Lactoyl-Glucosamine 50 g of liquid process flavour as described in example 2 were washed with 200 g ethyl acetate. The residue (approximately 17 g) was stirred with 70 g water. The non-soluble fraction was filtered off. The aqueous solution further was purified using preparative liquid chromatography carried out on a 150×21.2 mm ID 5 μm Hypercarb column (ThermoFinnigan, San Jose, Calif., USA). Gradient elution was carried out with lichrosolv grade water with 0.1% acetic acid (A) and lichrosolv grade methanol (B) (Merck, Darmstadt, Germany) as follows: 0-15 min 100% A, 15-17 min linear gradient to 100% B, 17-27 min 100% B, 27-29 min linear gradient back to 100% A (initial conditions), 29-35 min 100% A (re-equilibration) (%, v/v). The flow rate was 6 ml/min. For preparative LC a Gilson (Villiers le Bel, France) pump model 321 with a liquidhandler model 215 were used equipped with a UV detector (model UV/VIS-151) set at 276 nm.

0.8 g of aqueous solution was injected onto the system and a one-minute fraction, wherein a substance with the molecular weight. and MS fragmentation spectrum of N lactoyl-glucosamine was present, was collected at 14 min, freeze-dried and analyzed with NMR. The sample was confirmed to be pure N-lactoyl glucosamine.

The freeze-dried sample was diluted to 0.8 g in water and stored in the fridge.

Example 5

For a tasting session by a panel of experienced flavourists the following solutions were prepared:
1) A solution of 0.025% of a flavour composition as prepared in example 1 in tap water
2) A solution of 0.025% of a flavour composition as prepared in example 1 and 0.3% salt in tap water 3) A solution of 0.025% of a flavour composition as prepared in example 1, 0.3% salt and 0.03% mono sodium glutamate in tap water There was general agreement between the flavourists about the differences in taste between the samples:

Solution 1) had hardly any taste

Solution 2) had a metallic, bloody taste

Solution 3) had a very metallic, very bloody taste

Example 6

A group of experienced flavourists tasted a series of solutions containing 0.3% salt, 0.03% mono sodium glutamate, a standard roasted beef flavour and different concentrations of a flavour composition as prepared in example 1. Table 1 shows the amounts of flavour composition added to the solutions.

TABLE 1

| Solution | Amount of added flavour composition (wt %) |
|---|---|
| 1 | 0 |
| 2 | 0.006 |
| 3 | 0.012 |
| 4 | 0.018 |
| 5 | 0.025 |

There was general agreement between the flavourists about the differences in taste between the samples:

Solution 1: salty, umami;

Solution 2: salty, umami, slightly metallic, slightly bloody;

Solution 3: salty, umami, more bloody, medium tournedos;

Solution 4: salty, umami, more raw notes, medium rare tournedos; and

Solution 5: salty, umami, very metallic, very bloody, raw meat.

Example 7

For a tasting session by a panel of experienced flavourists a solution comprising 0.1 wt % of a flavour composition as prepared in example 4 in tap water was prepared. The panellists described the taste of the solution as strong metallic, bloody, raw meat like.

Example 8

Two samples were prepared as follow and compared:
Sample A: 0.6% of NaCl, 0.03% of MSG and 0.1% of HIT Duck Flavour (Quest)
Sample B: 0.6% of NaCl, 0.03% of MSG, 0.1% of HIT Duck Flavour (Quest) and 0.006% N Lactoyl glucosamine as prepared in example 4.

The samples were evaluated by a panel of experienced flavourists. There was general agreement about the difference in taste between the samples:
Sample A exhibited a savoury meaty taste with a recognizable duck meat flavour.
Sample B exhibited a savoury duck flavour, with slightly metallic taste, and more meaty character, authenticity, and naturalness than sample A.

The invention claimed is:

1. A flavour composition comprising at least 0.1 wt % of one or more flavouring substances and at least 0.001 wt % of one or more flavour modulating substances according to formula (I) or formula (II) or edible salts thereof or both:

$$R^1-CR^2(OR^3)-CO-NR^4-CHR^5R^6 \quad (I)$$

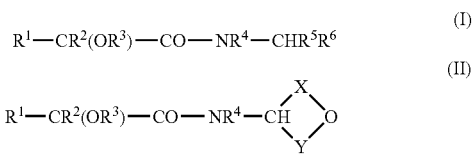

(II)

wherein:
$R^1$ and $R^2$ independently represent hydrogen; $C_1$-$C_8$ alkyl, $C_2$-$C_8$ alkenyl or $C_3$-$C_8$ cycloalkyl, each optionally substituted with 1-8 substituents selected from hydroxyl, oxo, $C_1$-$C_3$ alkoxyl, $C_1$-$C_3$ acyl, $C_1$-$C_3$ alkyl; $C_2$-$C_3$ alkenyl and $C_1$-$C_3$ carboxyl;
$R^3$ represents hydrogen, $C_1$-$C_3$ acyl or $C_1$-$C_3$ alkyl;
$R^4$ represents hydrogen; $C_1$-$C_6$ alkyl, $C_2$-$C_6$ alkenyl, $C_1$-$C_3$ acyl, $C_3$-$C_6$ cycloalkyl, $C_3$-$C_6$ cycloalkenyl or $C_1$-$C_6$ acyl, each optionally substituted with 1-6 substituents selected from hydroxyl, $C_1$-$C_3$ alkyl and $C_2$-$C_3$ alkenyl;
$R^5$ represents formyl;
$R^6$ represents $C_1$-$C_6$ alkyl wherein each carbon atom is substituted with a substituent independently selected from oxo, hydroxyl, $C_1$-$C_3$ alkoxyl, and $C_1$-$C_3$ acyl;
X represents —CHOH— or —CO—;
Y represents a moiety according to the formula —(CHOH)$_n$—CHR$^9$— wherein n is 1 or 2 and
wherein $R^9$ represents hydrogen or $C_1$-$C_4$ alkyl wherein each carbon atom is substituted with a substituent selected from hydroxyl, oxo, $C_1$-$C_3$ alkoxyl, and $C_1$-$C_3$ acyl.

* * * * *

UNITED STATES PATENT AND TRADEMARK OFFICE
CERTIFICATE OF CORRECTION

| | | Page 1 of 1 |
|---|---|---|
| PATENT NO. | : 8,053,013 B2 | |
| APPLICATION NO. | : 11/666532 | |
| DATED | : November 8, 2011 | |
| INVENTOR(S) | : Chris Winkel et al. | |

It is certified that error appears in the above-identified patent and that said Letters Patent is hereby corrected as shown below:

Face of Patent, Column 2, OTHER PUBLICATIONS, Line 6, delete "Backerial" and insert -- Bacterial --

Face of Patent, Column 2, OTHER PUBLICATIONS, Line 9, delete "Insolated" and insert -- Isolated --

Signed and Sealed this
Sixth Day of March, 2012

David J. Kappos
*Director of the United States Patent and Trademark Office*